United States Patent [19]
Chung

[11] Patent Number: 5,576,563
[45] Date of Patent: Nov. 19, 1996

[54] CHEMICAL PROBE FIELD EFFECT TRANSISTOR FOR MEASURING THE SURFACE POTENTIAL OF A GATE ELECTRODE IN RESPONSE TO CHEMICAL EXPOSURE

[75] Inventor: Young S. Chung, Gilbert, Ariz.

[73] Assignee: Motorola Inc., Schaumburg, Ill.

[21] Appl. No.: 427,389

[22] Filed: Apr. 24, 1995

[51] Int. Cl.$^6$ .......................... H01L 23/58; H01L 31/058
[52] U.S. Cl. ........................... 257/253; 257/467; 257/469
[58] Field of Search ................................. 257/253, 467, 257/469

[56] References Cited

U.S. PATENT DOCUMENTS 4,411,741  10/1983  Janata .

FOREIGN PATENT DOCUMENTS 5347339  12/1993  Japan .

OTHER PUBLICATIONS

Alvi et al, *Solid State Elec* vol. 31 No. 1, pp. 45–48 ©1988.
Muller et al, *Device Electronics for IC's*, pp. 443, 470, 471 ©1986.

*Primary Examiner*—Stephen Meier
*Attorney, Agent, or Firm*—Bruce T. Neel

[57] ABSTRACT

A chemical probe field effect transistor (10) for measuring surface potential as a function of temperature and used for chemical sensing. Source and drain regions (14, 16) in a semiconductor substrate (12) define a channel region (34). A gate insulating layer (18) covers the channel region, and a gate electrode layer (20) is disposed above the gate insulating layer to provide a gap (22) between the gate insulating layer and the gate electrode layer. This gap permits a fluid to contact an exposed surface (28) of the gate electrode layer. A heating layer (30) is disposed overlying the gate electrode layer to regulate its temperature. The surface potential of the gate electrode layer changes in response to the presence of certain chemicals in the contacting fluid.

20 Claims, 1 Drawing Sheet

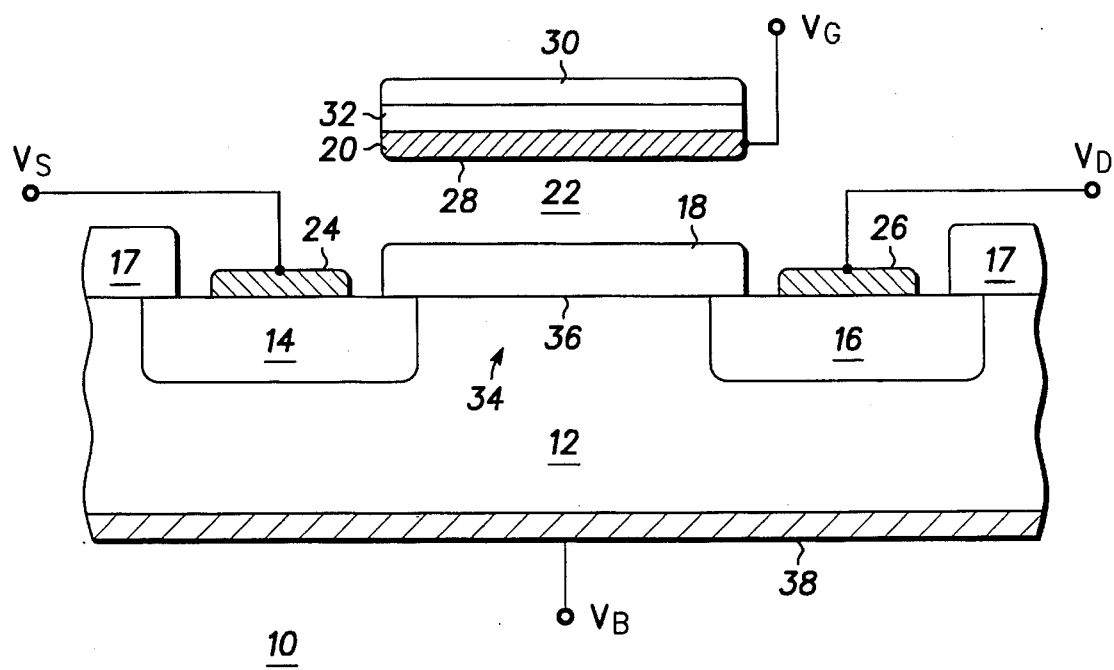

CHEMICAL PROBE FIELD EFFECT TRANSISTOR FOR MEASURING THE SURFACE POTENTIAL OF A GATE ELECTRODE IN RESPONSE TO CHEMICAL EXPOSURE

BACKGROUND OF THE INVENTION

The present invention relates, in general, to semiconductor devices and, more particularly, to a field effect transistor for measuring a change in surface potential as a function of temperature of the transistor's gate electrode due to exposure to a chemical as used in, for example, a chemical sensor.

Field effect transistors have been previously used in some cases as chemical sensors for measuring the concentration of a chemical in a fluid. One such prior sensor uses a gate electrode that is suspended over the channel region so as to provide a gap in which fluid may enter and contact an exposed surface of the gate electrode. A chemical in the fluid, to which the gate electrode is particularly sensitive, is adsorbed onto the exposed surface and changes the surface potential of the gate electrode. The drain current of the transistor changes in response to this surface potential change. Thus, if a constant gate voltage source is applied to the gate electrode during sensing, the change in drain current can be correlated to the concentration of the chemical in the fluid.

It has been found that the surface chemical reactions, which include adsorption/desorption reactions of the chemical to be sensed onto and off of the exposed gate electrode surface, of this prior sensor are very sensitive to temperature, so it is desirable that the temperature of the gate electrode be more directly regulated to optimize the output of the sensor. Also, it has been found to be desirable that this temperature be elevated above the ambient temperature to provide improved performance for the sensor. However, prior chemical sensors do not provide an integrated heating element for direct temperature control of the gate electrode. Instead, an external heater is required to heat the entire sensor assembly, rather than the gate electrode directly. Such an external heater is inconvenient to provide in a final, fully-manufactured chemical sensor assembly and increases the manufacturing cost thereof. Also, an external heater requires significant power consumption during operation.

Accordingly, there is a need for a chemical probe field effect transistor that includes a convenient and inexpensive heater that is directly incorporated into the sensor itself for direct, local heating of the sensor's gate electrode.

BRIEF DESCRIPTION OF THE DRAWING

The sole figure is a cross-sectional view of a chemical probe field effect transistor according to the present invention.

DETAILED DESCRIPTION OF THE DRAWING

Briefly stated, the present invention provides a field effect transistor for measuring a change in a surface potential of its gate electrode as a function of temperature when exposed to a fluid. As used herein, the term "fluid" includes both gaseous and liquid fluids. The transistor has a semiconductor substrate with a source region and a drain region disposed at the surface of the substrate. A channel region is defined between the source and drain regions, and a gate insulating layer is disposed overlying the surface of the substrate and between the source and drain regions. A gate electrode layer is disposed above the gate insulating layer and over the channel region, and a gap is provided between the gate insulating layer and the gate electrode layer that allows passage of the fluid onto an exposed surface of the gate electrode layer. According to the present invention, a heating layer is disposed overlying the gate electrode layer for direct temperature control of the gate electrode layer.

The present invention can be more fully described with reference to the sole figure, which is a cross-sectional view illustrating a field effect transistor 10. A substrate 12 has a source region 14 and a drain region 16 disposed at a surface 36 with a channel region 34 defined therebetween. A gate insulating layer 18 is disposed on surface 36 over channel region 34, and a metal layer 38 is disposed on a back surface of substrate 12 for providing a bulk potential bias $V_B$. An insulating layer 17 provides conventional isolation. A conventional source contact 24 is provided for applying a source potential $V_S$, and a conventional drain contact 26 is provided for applying a drain potential $V_D$.

A gate electrode layer 20 is disposed above gate insulating layer 18 to provide a gap 22. A fluid having a chemical concentration to be measured enters gap 22 and contacts a surface 28 of gate electrode layer 20. Gap 22 is provided to permit a fluid to come in contact with surface 28, and the dimensions of gap 22 may vary widely, but gap 22 preferably has a thickness between about 0.01 and 20 micrometers. During chemical sensing, a substantially constant gate potential $V_G$ or the equivalent is applied to gate electrode layer 20.

According to the present invention, a heating layer 30 is disposed overlying gate electrode layer 20. Heating layer 30 may be formed of numerous materials known in the art. For example, heating layer 30 can be an electrically resistive heater, and can be formed of polysilicon, nickel-chrome alloys, heavily-doped silicon, tantalum and its alloys, or platinum. An optional insulating layer 32 is provided to electrically isolate heating layer 30 from gate electrode layer 20 in those particular applications in which the specific material and technique used to provide heating layer 30 would electrically interfere with the application of a gate potential to gate electrode layer 20.

As will be appreciated by one of skill in the art, the desired chemical to be sensed will determine the material used for gate electrode layer 20, which in turn will determine whether optional insulating layer 32 is necessary. Heating layer 30 is preferably disposed sufficiently close to gate electrode layer 20 to permit uniform heating thereof. For example, heating layer 30 is preferably disposed less than about 50 microns above gate electrode layer 20. This distance is preferably determined by the thickness of optional insulating layer 32, when it is used. Additional details regarding the formation of one specific type of field effect transistor having a gate electrode layer separated from a substrate by a gap are described in U.S. Pat. No. 4,411,741 (issued to Janata on Oct. 25, 1983), which is hereby incorporated in full by reference. A significant advantage of the present invention is that the close proximity of heating layer 30 to gate electrode layer 20 will significantly reduce the power required by heating layer 30 during operation relative to the power required by prior sensors using an external heater.

Gap 22 may be formed using any of several well-known methods for providing an opening or void between two layers in a semiconductor device. Further, passages (not shown) correcting gap 22 to the external environment may be provided in a portion of gate electrode layer 20, or in other layers (not shown) of transistor 10 that are supporting gate electrode layer 20, to permit passage of an external fluid into gap 22.

Although a specific transistor is illustrated in the sole figure, one of skill in the art will recognize that the present invention can be applied to a wide variety of field effect transistors. However, as a specific, non-limiting example of transistor 10, substrate 12 is a P-type (100) silicon substrate having N-type source and drain regions 14 and 16. Gate insulating layer 18 is a thermally grown and/or deposited silicon oxide layer. Alternatively, gate insulating layer 18 may be a nitride layer or an oxide/nitride layer. The material selected for gate electrode layer 20 depends, in part, on the target chemical concentration to be measured in the fluid contacting surface 28. As is known, this material may preferably be a noble metal or one of it alloys or alternatively a transition metal or one of its alloys. As a particular example, if the concentration of phosphine in a fluid is to be sensed, then gate electrode layer 20 is preferably an alloy of gold and palladium. Also, this material can be a conducting or semiconducting metal oxide, as is also known.

As is known, the surface potential of gate electrode layer 20 at surface 28 varies due to the surface reaction of chemicals onto surface 28 from a fluid within gap 22. As is also known, this change in surface potential changes the electric potential between surface 28 of gate electrode layer 20 and channel region 34 of substrate 12 thereby altering the impedance of transistor 10 in channel region 34. As a result, the drain current of transistor 10 is modulated by the surface chemical reaction on surface 28. By applying a substantially constant gate potential bias $V_G$ or the equivalent to gate electrode layer 20, the variation in drain current can be directly related to a chemical concentration in the fluid being measured. Additional details regarding the effect of an adsorbed chemical onto the gate electrode of a field effect transistor are described in U.S. Pat. No. 4,411,741, which was incorporated by reference above.

The change in surface potential of gate electrode layer 20 in response to a reacted chemical is very sensitive to the temperature of surface 28. Specifically, the magnitude of this surface potential change is exponentially related to the inverse of this surface temperature. Thus, it is preferable that gate electrode layer 20 be maintained at a controlled temperature during sensing. This is accomplished with heating layer 30 using conventional control techniques to regulate this temperature. In general, this temperature is controlled to between just above ambient temperature and about 1,000° C. As a specific example, if phosphine is to be continuously sensed by transistor 10, gate electrode layer 20 is maintained at a temperature of about 100° C. by heating layer 30.

In addition to maintaining gate electrode layer 20 at a controlled temperature, heating layer 30 also preferably regulates gate electrode layer 20 at an elevated temperature. This is desired because the rate of the adsorption reaction of the chemical being sensed on surface 28 is typically too dominant at ambient temperatures, which causes the responsiveness of the chemical sensor to be reduced with repeated or continuous exposure to the chemical. The use of an elevated temperature regenerates surface 28 in preparation for sensing changes in chemical concentration because the elevated temperature causes desorption of the previously-sensed chemical from surface 28. If the temperature of surface 28 is too low, then this desorption rate is too slow and the recovery time of the sensor is increased. As a specific example of this regeneration, gate electrode layer 20 may be heated to a temperature of about 200° C. for about 2 minutes when sensing phosphine. This temperature is above the optimum temperature of about 100° C. preferably used during the sensing of phosphine, which is discussed in detail below.

As will be recognized by one of skill in the art, there is an optimum, elevated temperature for gate electrode layer 20 that depends on the chemical to-be sensed and the material used to form gate electrode layer 20. This optimum temperature depends on the particular application desired. For example, the optimum temperature for continuous monitoring corresponds to a substantial equilibrium of the adsorption and desorption reactions on surface 28. Below this optimum temperature, the sensitivity of the sensor tends to degrade with repeated exposure to the chemical being sensed because the desorption reaction is too slow and eventually causes a saturation of the chemical on surface 28. On the other hand, above this optimum temperature, the desorption rate of the chemical being sensed becomes too great to allow meaningful measurement. As an example, if phosphine is being sensed using a gold-palladium alloy, then the optimum temperature for continuous monitoring is about 100° C. The optimum temperature for other chemicals and/or applications can be readily determined by simple experimentation.

By now, it should be appreciated that there has been provided a novel field effect transistor for chemical sensing. This transistor has the advantages of providing direct temperature control of the gate electrode of the transistor by an integrated heating element during sensing. This integrated heater avoids the need for external heaters as required in prior sensors. Another advantage of the heater of the present invention is that it can be directly incorporated into the manufacturing process used to form the sensor itself, thereby dramatically reducing the cost to manufacture a chemical sensor that includes a heating element. In addition, this integrated heating element permits the temperature control of the gate electrode to an extent that makes it feasible to optimize chemical sensing with respect to sensor sensitivity, selectivity, and stability. Further, it is an advantage that the integrated heating element greatly reduces power consumption.

The foregoing discussion discloses and describes merely exemplary methods and embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

I claim:

1. A field effect transistor for measuring a change in a surface potential of a gate electrode of said transistor exposed to a fluid, comprising:

a semiconductor substrate having a first surface;

a source region and a drain region disposed at said first surface of said semiconductor substrate;

a channel region defined between said source region and said drain region;

a gate insulating layer overlying said first surface of said semiconductor substrate and disposed between said source region and said drain region;

a gate electrode layer, having a second surface facing said gate insulating layer, disposed above said gate insulating layer and over said channel region, wherein a gap is provided between said gate insulating layer and said gate electrode layer that allows passage of said fluid onto said second surface of said gate electrode layer; and a heating layer disposed overlying said gate electrode layer wherein said heating layer and said gate electrode layer are controlled by separate voltages.

2. The transistor of claim 1 wherein said heating layer is disposed directly on said gate electrode layer.

3. The transistor of claim 1 further comprising a second insulating layer disposed on said gate electrode layer and wherein said heating layer is disposed on said second insulating layer.

4. The transistor of claim 1 wherein said heating layer is an electrically resistive heater.

5. The transistor of claim 1 wherein said heating layer is polysilicon.

6. The transistor of claim 1 wherein said heating layer is heavily-doped silicon.

7. The transistor of claim 1 wherein said heating layer comprises a material selected from the group consisting of nickel-chrome alloys, tantulum and its alloys, and platinum.

8. The transistor of claim 1 wherein said gate electrode layer is selected from the group consisting of a noble metal and its alloys, and a transition metal and its alloys.

9. The transistor of claim 1 wherein said gate electrode layer is selected from the group consisting of a conducting metal oxide and a semiconducting metal oxide.

10. The transistor of claim 1 wherein said gate electrode layer is an alloy of gold and palladium.

11. The transistor of claim 10 wherein said fluid comprises phosphine.

12. The transistor of claim 11 wherein said gate electrode layer is controlled at a temperature of about 100° C. by said heating layer.

13. A field effect transistor for detecting a concentration of a component in a fluid, comprising:

a semiconductor substrate having a first surface;

a source region and a drain region disposed at said first surface of said semiconductor substrate;

a channel region defined between said source region and said drain region;

a gate insulating layer overlying said first surface of said semiconductor substrate and disposed between said source region and said drain region;

a gate electrode layer, having a second surface facing said gate insulating layer, disposed above said gate insulating layer and over said channel region, wherein a gap is provided between said gate insulating layer and said gate electrode layer that allows passage of said fluid onto said second surface of said gate electrode layer and an adsorption of said fluid at said second surface of said gate electrode layer modulates a drain current through said channel region; and a heating layer disposed overlying said gate electrode layer wherein said heating layer and said gate electrode layer are controlled by separate voltages.

14. The transistor of claim 13 wherein said heating layer regulates a temperature of said gate electrode layer to control a reaction rate of adsorption and desorption of said fluid from said second surface of said gate electrode layer.

15. The transistor of claim 13 wherein said heating layer is disposed less than about 50 microns above said gate electrode layer.

16. The transistor of claim 13 wherein said gate electrode layer is regenerated at an elevated temperature.

17. The transistor of claim 13 wherein said gate electrode layer is an alloy of gold and palladium.

18. The transistor of claim 17 wherein said fluid comprises phosphine.

19. The transistor of claim 18 wherein said gate electrode layer is controlled at a temperature of about 100° C. by said heating layer.

20. The transistor of claim 13 wherein said gate electrode layer is selected from the group consisting of a conducting metal oxide and a semiconducting metal oxide.

\* \* \* \* \*